United States Patent [19]

Toja et al.

[11] Patent Number: 5,183,896
[45] Date of Patent: Feb. 2, 1993

[54] NEW DERIVATIVES OF 1,2,5,6-TETRAHYDROPYRIDIN-3-CARBOXALDEHYDE OXIME

[75] Inventors: Emilio Toja, Milan; Carla Bonetti, Fontanella; Fernando Barzaghi; Giulio Galliani, both of Monza, all of Italy

[73] Assignee: Roussel Uclaf, Paris, France

[21] Appl. No.: 666,515

[22] Filed: Mar. 11, 1991

[30] Foreign Application Priority Data

Mar. 14, 1990 [IT] Italy .................. 19675 A/90

[51] Int. Cl.⁵ .......................................... C07D 211/68
[52] U.S. Cl. ................... 546/326; 546/281; 546/193; 546/194; 544/365; 544/131
[58] Field of Search ........... 546/326, 281, 193, 194; 544/365, 131; 514/354, 343, 318, 255, 237.2

[56] References Cited

U.S. PATENT DOCUMENTS

| | | | |
|---|---|---|---|
| 3,004,979 | 10/1961 | Druey et al. | 546/333 |
| 4,710,508 | 12/1987 | Bergmeier et al. | 514/357 |
| 4,786,648 | 11/1988 | Bergmeier et al. | 514/357 |
| 4,902,699 | 2/1990 | Toja et al. | 514/357 |
| 4,921,868 | 5/1990 | Galliani et al. | 546/326 |
| 5,015,655 | 5/1991 | Galliani et al. | 514/413 |
| 5,053,416 | 10/1991 | Toja et al. | 514/340 |

OTHER PUBLICATIONS

Thompson et al. The New England Journal of Medicine Aug. 16, vol. 323. No. 7, 1990.
Raymond T. Bartus, et al "The Cholinergic Hypothesis of Geriatric Memory Dysfunction"*Science* vol. 217, No. 30, Jul. 1982, pp. 408–417.
Galliani et al, "Pharmacological Profile of RU 35963, A New Muscarinic Agonist." *European Journal Of Pharmacology* vol. 183 (1990) pp. 1940–1941.
Toja et al, "Amnesia-Reversal Activity of a Series of 5-Alkoxy-1-Arylcarbonyl-2-Phrrolidinones and 5-Alkoxy-1-Arylmenthyl-2-Pyrrolidinones." *European Journal Medicine Chemistry* (1991) 26, pp. 415–422.
7560849 Jul. 31, 1990 Galliani et al. (Pending U.S. patent application.)

*Primary Examiner*—Jane T. Fan
*Attorney, Agent, or Firm*—Stevens, Davis, Miller & Mosher

[57] ABSTRACT

Compounds of the formula

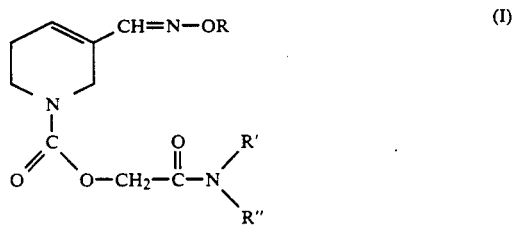

which have a long-lasting cholinomimetic activity by oral route. Also disclosed are methods for preparing the compounds and pharmaceutical compositions containing the compounds.

11 Claims, No Drawings

NEW DERIVATIVES OF 1,2,5,6-TETRAHYDROPYRIDIN-3-CARBOXALDEHYDE OXIME

The present invention relates to new derivatives of 1,2,5,6-tetrahydropyridin-3-carboxaldehyde oxime, their preparation process and their use as medicaments.

A subject of the invention is the compounds of formula (I):

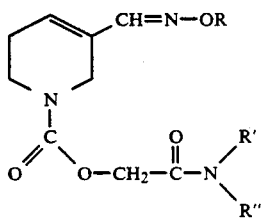

in which

-R represents hydrogen, a linear, branched or cyclic alkyl, alkenyl or alkynyl which contains up to 8 carbon atoms, -R' and R", identical or different from each other, represent hydrogen, a linear, branched or cyclic alkyl, alkenyl or alkynyl containing up to 8 carbon atoms, or form together with the nitrogen atom to which they are linked a heterocyclic radical.

When R, R' or R" represents a linear or branched saturated alkyl, it is preferably methyl, ethyl, propyl, isopropyl, butyl, sec-butyl isobutyl, pentyl, hexyl, tert-butyl, tert-pentyl, neopentyl or hexyl.

When R, R' or R" represents an unsaturated aliphatic alkyl, it is preferably an ethylenic radical such as, for example, vinyl, allyl, 1,1,-dimethylallyl, 2-butenyl radical, or acetylenic such as, for example, ethynyl or propynyl.

When R, R' or R" represents a cyclic alkyl, it is preferably cyclopropyl, cyclobutyl, cyclopentyl, cyclohexyl, cyclopropylmethyl, cyclobutylmethyl, cyclopentylmethyl or cyclohexylmethyl.

When R' and R" form with the nitrogen atom to which they are linked a heterocyclic, it can be a heterocycle containing this single nitrogen atom as the only heteroatom, it can for example be piperidinyl or pyrrolidinyl ring, it can also be a heterocycle containing a second heteroatom, for example a heterocycle containing a second nitrogen atom, or also a heterocycle containing an oxygen or sulphur atom, for example a piperazinyl or morpholinyl ring optionally substituted by an alkyl radical containing up to 4 carbon atoms.

Among the preferred products of the invention, there can be mentioned:

the compounds of formula (I) in which R represents a linear alkyl containing up to 8 carbon atoms, for example methyl, the compounds of formula (I) in which R' and R", being identical, represent alkenyl containing up to 4 carbon atoms, for example an allyl radical, the products of formula (I) in which R' and R" form with the nitrogen atom to which they are linked piperidinyl, piperazinyl or N-methyl piperazinyl, and notably the product of Example 3.

The compounds of the invention have very useful pharmacological properties and notably a significant long-lasting cholinomimetic activity by oral route.

It is well known that learning and memory disorders in old people are especially linked to a deficiency in the central cholinergic system, in particular in senile dementia and Alzheimer's disease.

It is therefore evident that products having a central cholinergic action can be employed in the therapeutic treatment of these illnesses (Bartus, R.I., Science 217, 408, 1982).

It has been demonstrated that arecoline injected by intravenous route has a positive effect on patients who have a memory deficiency (Sitaram N. et al., Science 201, 274, 1978) (Christie J.E. et al., Brit. J. Psychiatry 138, 46, 1981).

A limitation of the therapeutic use of arecoline is linked to the fact that this product has a very weak activity by oral route and a short-term action.

The products which are a subject of the invention demonstrated, after administration by oral route, a central cholinomimetic activity higher than that of arecoline and a longer-lasting action.

Therefore, a subject of the invention is the products of the invention as medicaments, notably useful in the treatment of Alzheimer's disease or senile dementia and also in the treatment of memory disorders of the aged.

A particular subject of the invention is the preferred compounds mentioned above as medicaments, and notably the compounds of the examples.

A more particular subject of the invention is the product of Example 3 as a medicament.

The usual dosage varies according to the affection in question, the patient being treated and the administration route. 1The posology can be comprised between 1 mg and 100 mg/day, for example, between 1 and 15 mg/day in one or more doses for the product of Example 3 administered by oral route.

Also a subject of the present invention is the pharmaceutical compositions containing as the active ingredient at least one product of formula (I). The pharmaceutical compositions of the invention can be solid or liquid and can be presented in the pharmaceutical forms currently used in human medicine, such as for example, plain or sugar-coated tablets, capsules, granules, suppositories, injectable preparations; they are prepared according to the usual methods.

The active ingredient or ingredients can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The products of the invention have the not insignificant advantage of being stable in aqueous medium.

Also a subject of the invention is a preparation process characterized in that a compound of formula (II):

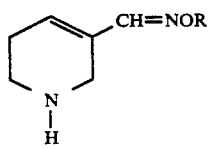

in which R has the same meaning as above, is subjected to the action of a compound of formula (III):

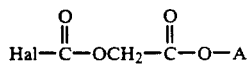

(III)

in which A represents a protector group of the acid function, and Hal represents a halogen atom, in order to obtain the compound of formula (IV):

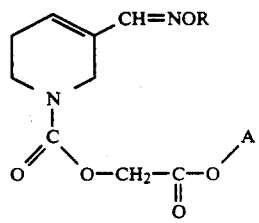

(IV)

which is subjected to the action of a cleaving agent of the protector group, in order to obtain the acid of formula (V):

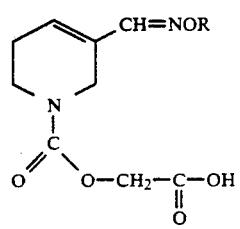

(V)

then a functional derivative of this acid (V) is subjected to the action of an amine of formula (VI):

in which R' and R" keep the same meaning as above, in order to obtain the corresponding compound of formula (I).

In a preferred method for implementing the invention, A represents benzyl, optionally substituted by $NO_2$;

Hal represents a chlorine atom, the reaction of the compound of formula (II) with the compound of formula (III) takes place in the presence of a base such as, for example, triethylamine in an inert solvent such as for example benzene or dichloromethane, the cleaving agent of the paranitrobenzyl protector group is sodium sulphide in aqueous solution to which an organic solvent is added, for example tetrahydrofuran, the reaction of the compound of formula (V) with the compound of formula (VI) takes place after conversion of the acid function into chloride, by the action of thionyl chloride in chloroform.

The compounds of formula (II) are known products described in the European Patent 239445.

The compounds of formula (III) are new products which can be prepared as indicated hereinafter in the experimental part. This preparation can be summarized by the following reaction diagram:

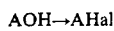

AOH→AHal

The products AOH and notably 4-nitrobenzyl hydroxyacetate can be prepared according to the process described in CA 61, 4469g; Izv. AKAD. NAUK. SSSR Ser. Khim (1964) pages 685–692.

The following examples illustrate the invention without however limiting it.

Preparation: 4-nitrobenzyl chlorocarbonyloxyacetate 17.8 g of phosgene are introduced into 60 cm$^3$ of benzene then a suspension of 7.1 g 4-nitrobenzyl hydroxyacetate (Izv. Akad. Nauk. SSSR. Khim 1964 (4) 685–692, Chem. Abst 61, 4469g) in 150 cm$^3$ of benzene. The mixture is agitated for 2 hours at ambient temperature, brought to 7°/8° C. and 5.16 cm$^3$ of diazabicycloundecene is added. After maintaining for one hour at this temperature, the mixture is decanted and the supernatant phase is partially concentrated under reduced pressure at 30°/35° C. until about 30 cm$^3$ is obtained and the product is used as it is for the following stage.

EXAMPLE 1

(aminocarbonyl) methyl 3-(methoxyiminomethyl)-1,2,5,6-tetrahyiro-pyridine-1-carboxylate Stage A: (4-nitrobenzyl)-methyl 3-(methoxyiminomethyl)-1,2,5,6-tetrahydro-pyridine-1-carboxylate 1.66 g of 1,2,5,6-tetrahydropyridin-3-carboxaldehyde-O-methyl oxime is introduced under an inert atmosphere into 30 cm$^3$ of benzene, 1.65 cm$^3$ of triethylamine is added, followed by cooling down to a temperature of between 7° and 13° C., and the reaction medium obtained is added to the above preparation. The suspension is agitated for one hour at ambient temperature and left for 16 hours. The reaction medium is washed with a 5% aqueous solution of hydrochloric acid, the aqueous phase is separated out which is extracted with ethyl acetate, the organic phases are reunited, dried and the solvents are evaporated under reduced pressure. The residue is chromatographed on silica eluant: cyclohexane - ethyl acetate 3-2). After crystalization from ethyl acetate - cyclohexane, 3.95 g of expected product is obtained.

M.P.=93°–94° C.

Analysis: $C_{17}H_{19}N_3O_7$: 377.353;

Calculated: C%, 54.11; H%, 5.08; N%, 11.14.

Found: C%, 54.28 H%, 5.16 N%, 10.88.

Stage B: [(3-methoxyiminomethyl)-1,2,5,6-tetrahydropyridin-1-yl-carbonyl]-oxy acetic acid 5.63 g of the product obtained in Stage A is introduced into 130 cm$^3$ of tetrahydrofuran and 70 cm$^3$ of water. After cooling down to 0° C., 3.58g of nonahydrated sodium sulphide in 70 cm$^3$ of water is added. The mixture is agitated for one hour at this temperature, 11.3 cm$^3$ of N hydrochloric acid is added, the tetrahydrofuran is evaporated off and extraction is done with ethyl acetate and p-nitrothiobenzyl alcohol. Acidification is carried out with 2N hydrochloric acid, then extraction with ethyl acetate, and the extracts are dried over sodium sulphate and evaporated. After crystallization from ethyl acetate diisopropyl ether, 3.25 g of expected product is obtained. M.p. =133–134° C. (decomposition).

Analysis: $C_{10}H_{14}N_2O_5$: 242.231
Calculated: C%, 49.59; H%, 5.83; N%, 11.57,
Found: C%, 49.55, H%, 5.91; N%, 11.44, Stage C:

[[(3-methoxyiminomethyl)-1,2,5,6-tetrahydro-pyridin-1-yl-carbonyl]-oxy]-acetic acid chloride 1.5 g of acid obtained above and 4.5 cm³ of thionyl chloride in 15 cm³ of chloroform are heated for 30 minutes under reflux. The excess thionyl chloride and the solvent are eliminated under reduced pressure. The residual oil is used as it is for the following stage.

Stage D: (aminocarbonyl)-methyl 3-(methoxyiminomethyl)-1,2,5,6-tetrahydropyridine-1-carboxylate

[[(3-methoxyiminomethyl)-1,2,5,6-tetrahydropyridin-1-yl-carbonyl]-oxy] acetic acid chloride is prepared again as indicated in Stage C starting with 1.1 g of acid obtained in Stage B and 3.3 cm³ of thionyl chloride The residual oil is taken up in 10 cm³ of chloroform and poured into a solution containing 0.7 g of ammonia in 20 cm³ of chloroform. The suspension is agitated for one hour and 30 minutes, washed with water, the aqueous phase is separated out and extracted with ethyl acetate, dried and evaporated. The residue is chromatographed on silica (eluant: chloroform-methanol 9-1) and 0.65 g of expected product is obtained which is added to 0.95 g of product obtained during a previous preparation and diluted with benzene. 1.45 g of expected product is obtained. M.p. = 131–133° C.

Analysis: $C_{10}H_{15}N_3O_4$: 241.247
Calculated: C%, 49.79;H%, 6.27, N%, 17.42,
Found: C%, 49.64.H%, 6.25; N%, 17.17,

EXAMPLE 2

(diethylaminocarbonyl) methyl 3-(methoxyiminomethyl)-1,2,5,6-tetrahydropyridine-1-carboxylate The operation is carried out as in Stage C of Example 1 starting with 1.5 g of acid obtained in Stage B of Example 1. The residual oil is taken up in 20 cm³ of benzene, and poured into a solution containing 1.3 cm³ of diethylamine in 20 cm³ of benzene (exothermic reaction). After agitating for 30 minutes at ambient temperature, and washing with water, the aqueous phase is separated out and extracted with ethyl acetate, the organic phases are reunited, dried and evaporated to dryness. The residue is chromatographed on silica (eluant: ethyl acetate) and 1.35 g of expected product is recovered which is taken up in hexane. M.p. = 83–84° C.; insoluble in $H_2O$, 2N NaOH, 2N HCl.

Analysis: $C_{14}H_{23}N_3O_4$: 297.355;
Calculated C%, 56.55;H%, 7.80; N%, 14.13;
Found: C%, 56.51; H%, 7.82;N%; 14.02;

EXAMPLE 3

(di(2-propenyl)-aminocarbon-yl)-methyl 3-(methoxyiminomethyl)-1,2,5,6-tetrahydropyridine-1-carboxylate The operation is carried out as in Stage C of Example 1 starting with 1.5 g of acid obtained in Stage B of Example 1. The residual oil is taken up in 20 cm³ of benzene and poured into a solution containing 1.58 cm³ of di-allylamine in 20 cm³ of benzene. The synthesis is continued as indicated in Example 2. After chromatography on silica (eluant: ethyl acetate - n-hexane 7-3), 1.85 g of yellow oil is recovered which is taken up in hexane and precipitated with ether. 1.75 g of crystallized product is collected.

M.p. = 63.5–64° C.; insoluble in $H_2O$, 2N HCl, 2N NaOH.

Analysis: $C_{16}H_{23}N_3O_4$: 321.377
Calculated: C%; 59.80;H%; 7.21; N%; 13.08,
Found: C%, 59.58.; H%, 7.18; N%, 12.99

EXAMPLE 4

(1-piperidinylcarbonyl)-methyl 3-(methoxyiminomethyl)-1,2,5,6-tetrahydropyridine-1-carboxylate The operation is carried out as in Stage C of Example 1 starting with 2 g of acid obtained as in Stage B of Example 1 and 6 cm³ of thionyl chloride. The residual oil is taken up in 20 cm³ of benzene, and poured into a solution containing 1.65 cm³ of piperidine (exothermic reaction). The synthesis is continued as indicated in Example 2. The residue obtained before chromatography is crystallized from aqueous ethanol after chromatography on activated charcoal. The product obtained is chromatographed on silica (eluant: ethyl acetate), concentrated to dryness, taken up in ether and 2.12 g of expected product is obtained M.p. = 93–94° C.; insoluble in $H_2O$, 2N HCl, 2N NaOH.

Analysis: $C_{15}H_{23}N_3O_4$: 309.366
Calculated: C%; 58.24; H%; 7.49; N%, 13.58
Found: C%, 57.97; H%, 7.57; N%, 13.38.

EXAMPLE 5

(4 methyl-1-piperazinyl)-carbonylmethyl 3-(methoxyiminomethyl)-1,2,5,6-tetrahydropyridine-1-carboxylate The operation is carried out as in Stage C of Example 1 starting with 1.45 g of acid obtained as in Stage B of Example 1 and 4.4 cm³ of thionyl chloride The residual oil is taken up in 20 cm³ of benzene, poured into a solution containing 1.34 cm³ of N-methyl piperazine in 20 cm³ of benzene and agitated for one hour and 30 minutes at ambient temperature. After washing with water, the aqueous phase is separated out, neutralized with 5% sodium bicarbonate and extracted with ethyl acetate. After chromatography on silica (eluant: chloroform - methanol 9-1) 1.45 g of oil is obtained which is crystallized by precipitation in n-hexane and 1.25 g of expected product is obtained. M.p. =104–105° C.; soluble in water, 2N HCl, insoluble in 2N NaOH.

Analysis: $C_{15}H_{24}N_4O_4$: 324.381;
Calculated: C%; 55.54; H%; 7.46; N%; 17.2;
Found: C%; 55.28; H%, 7.34; N%, 17.07.

EXAMPLE 6

Tablets were prepared corresponding to the following formula

| | |
|---|---|
| Compound of Example 3 | 50 mg |
| Excipient, sufficient quantity for a tablet completed at | 300 mg |

(Detail of excipient: lactose, wheat starch, treated starch, rice starch, talc, magnesium stearate).

EXAMPLE 7

Capsules were prepared corresponding to the following formula:

| Product of Example 3 | 60 mg |
|---|---|
| Excipient, sufficient quantity for a capsule completed at | 300 mg |

(Detail of excipient: talc, magnesium stearate, aerosil).

PHARMACOLOGICAL STUDY

Acute toxicity

The test is carried out on male mice (CD1 Charles Rivers) weighing 22 to 24 g, which have gone without food for 16 hours. The products are administered by oral route at a dose of 1000, 500, 250 and 125 mg/kg. The mortality is noted over the 7 days following the treatment.

| Product of Example 3 | $LD_{50} = 500$ mg/kg |
|---|---|
| Arecoline, HBr | $LD_{50} = 600$ mg/kg |

1Test of the isolated ileum of a guinea pig

Ileum fragments are removed from a guinea-pig killed by decapitation. The isolated ileum is placed in 10 $cm^3$ of Tyrode solution at 37° C. and aerated by a mixture of oxygen (95%) and carbon dioxide (5%). Contractions caused by the products are recorded using a sensor connected to a polygraph. The products under test are added, at concentrations comprised between $1.10^{-3}$ M and $1.10^{-8}$ M/1.

The products showing a contracturating effect are tested relative to atropine and hexamethonium in order to establish whether the activity is of "muscarinic" or "nicotinic" type.

The agonist activity is expressed in $pD_2$ (negative logarithm of the dose which produces 50% of the maximum effect).

| Product of Example 3 | $pD_2 < 4$ |
|---|---|
| Arecoline, HBr | $pD_2 = 6.90$ |

Diarrheic activity

The test is carried out on male mice ($CD_1$ Charles Rivers) weighing 25 to 30 g, which have gone without food for 6 hours. The product dissolved at 5% in methocel is administered by oral route, using a probang.

The control animals receive only the excipient.

After treatment, the animals are put separately in cages. The bottoms of the cages are covered with blotting paper and are observed at 30, 60, 120 and 180 minute intervals.

The absorbent sheets of paper are changed after each observation.

The consistency of the faeces is evaluated according to the method of Randall and Baruth (Arch. Int. Pharmacodyn. 220, 94, 1976) by following the scale of the following values:

0: firm consistency,
1: slightly soft feces with or without moist ring,
2: slightly soft feces with presence of a well-defined moist circle,
3: soft feces with presence of a large moist circle,
4 feces without consistency with presence of a very large moist circle.

For each product, the dose was noted which caused diarrhoea in 50% of the animals according to the method of Miller and Tainter (Proc. Soc. Exp. Biol. Med., 57 261, 1944).

| Product of Example 3 | $DE_{50} > 50$ |
|---|---|
| Arecoline, HBr | $DE_{50}$ 35 |

Hypothermic activity.

The test is carried out on male mice ($CD_1$ Charles Rivers) weighing 25 to 30 g, which have gone without food for 6 hours.

The body temperature is noted using a thermocouple placed about 1.5 $cm^3$ inside the rectum and connected to an electrical temperature recorder.

The products are administered by oral or sub-cutaneous route and the temperatures are noted at 0 and 30 minutes, 1 hour, 2 hours and 2 and a half hours after treatment.

The degree of hypothermia is evaluated as the difference between the treated animals and the control animals and the dose necessary to reduce the body temperature by 1° C. is determined.

| Example | Effective dose (−1° C. in mg/kg) | |
|---|---|---|
| | O Route | SC Route |
| 3 | 9 | 8 |
| Arecoline, HBr | 190 | 3 |

The duration of action of the products is determined by using doses which can reduce the temperature by 1.5° C. to 1.7° C.

| | | | Variations in body temperature (°C.) | | | | |
|---|---|---|---|---|---|---|---|
| | dose | adminis- | treatment time in minutes | | | | |
| Example | mg/kg | tration | 0 | 30 | 60 | 120 | 180 |
| 3 | 15 | os | +0.1 | −1.3** | −1.7** | −0.5 | +0.1 |
| | 12 | sc | ±0 | −0.9** | −1.6** | −0.6 | ±0 |
| Arecoline HBr | 3.5 | sc | −0.1 | −1.5** | −0.1 | +0.2 | +0.2 |

**Values significantly different from the controls (p < 0.01).

We claim:

1. A compound of formula I

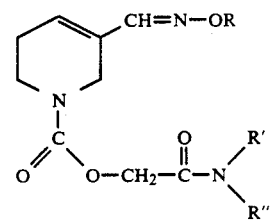

in which: R represents hydrogen, a linear, branched or cyclic alkyl, alkenyl or alkynyl containing up to 8 carbon atoms, and R' and R" are identical or different from each other, and represent a hydrogen, a linear, branched or cyclic alkyl, alkenyl or alkynyl containing up to 8 carbon atoms, or form together with the nitrogen to which they are linked a heterocyclic radical selected from the group consisting of piperidinyl, piperazinyl, N-methyl piperazinyl and morpholinyl, said morpholinyl being optionally substituted by an alkyl radical containing up to 4 carbon atoms.

2. The compound of formula (I) defined in claim 1, in which R represents a linear alkyl containing up to 8 carbon atoms.

3. The compound of formula (I) defined in claim 2, in which R represents methyl.

4. The compound of formula (I) as defined in claim 1 in which R' and R" are identical and represent an alkenyl containing up to 4 carbon atoms.

5. The compound of formula (I) as defined in claim 2 in which R' and R" are identical and represent an alkenyl containing up to 4 carbon atoms 6. The compound of formula (I) as defined in claim 3 in which R' and R" are identical and represent an alkenyl containing up to 4 carbon atoms.

7. The compound of formula (I) as defined in any of claims 4–6 in which R' and R" represent allyl.

8. The compound (di(2-propenyl)-aminocarbonyl)-methyl 3-(methoxyiminomethyl)-1,2, 5,6-tetrahydropyridine-1-carboxylate.

9. The compound of formula (I) as defined in claim 1 in which the radical R' and R" form together with the nitrogen atom to which they are linked a heterocyclic radical selected from the group consisting of piperidinyl, piperazinyl and N-methyl piperazinyl.

10. The compound of formula (I) as defined in claim 2 in which the radical R' and R" form together with the nitrogen atom to which they are linked a heterocyclic radical selected from the group consisting of piperidinyl, piperazinyl and N-methyl piperazinyl.

11. The compound of formula (I) as defined in claim 3 in which the radical R' and R" form together with the nitrogen atom to which they are linked a heterocyclic radical selected from the group consisting of piperidinyl, piperazinyl and N-methyl piperazinyl.

* * * * *